United States Patent [19]

Treuner

[11] 4,052,393
[45] Oct. 4, 1977

[54] 4-SUBSTITUTED DERIVATIVES OF PYRAZOLO [1,5-a]-QUINOXALINE-3-CARBOXYLIC ACIDS AND ESTERS

[75] Inventor: Uwe D. Treuner, Regensburg, Germany

[73] Assignee: E. R. Squibb & Sons, Inc., Princeton, N.J.

[21] Appl. No.: 669,114

[22] Filed: Mar. 22, 1976

Related U.S. Application Data

[63] Continuation-in-part of Ser. No. 628,277, Nov. 3, 1975, Pat. No. 3,994,893.

[51] Int. Cl.² .................. C07D 487/04; A61K 31/495
[52] U.S. Cl. ........................... 260/250 Q; 544/115; 424/248.52; 424/248.55; 424/248.53
[58] Field of Search .................. 260/250 Q, 250 QN

[56] References Cited
U.S. PATENT DOCUMENTS 3,369,897  2/1968  Menzel et al. ............... 96/56.5
3,994,893  11/1976  Treuner et al. ............... 260/250 Q Primary Examiner—Donald G. Daus
Assistant Examiner—Mark L. Berch
Attorney, Agent, or Firm—Lawrence S. Levinson; Merle J. Smith

[57] ABSTRACT

New 4-substituted derivatives of pyrazolo[1,5-a]-quinoxaline-3-carboxylic acid, esters and their salts have the formula

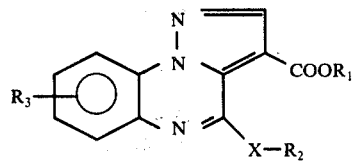

$R_1$ is hydrogen, lower alkyl or a salt forming ion; $R_2$ is hydrogen, lower alkyl, phenyl-lower alkylene or amino-lower alkylene; $R_3$ is hydrogen, lower alkyl, halogen or lower alkoxy; and X is oxygen or sulfur.

The new compounds are useful as anti-inflammatory agents.

12 Claims, No Drawings

4-SUBSTITUTED DERIVATIVES OF PYRAZOLO [1,5-a]-QUINOXALINE-3-CARBOXYLIC ACIDS AND ESTERS

This application is a continuation-in-part of application Ser. No. 628,277, filed Nov. 3, 1975, U.S. Pat. No. 3,994,893, Nov. 30, 1976.

SUMMARY OF THE INVENTION

This invention relates to new 4-substituted derivatives of pyraxolo [1,5-a]quinoxaline-3-carboxylic acids and esters which have the formula

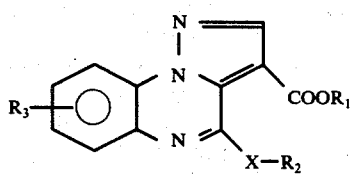

(I)

wherein $R_1$ is hydrogen or lower alkyl; $R_2$ is hydrogen, lower alkyl, phenyl-lower alkylene or an amino-lower alkylene group, i.e.,

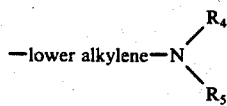

wherein $R_4$ and $R_5$ each is hydrogen or lower alkyl or together with the nitrogen complete an unsubstituted or substituted pyrrolidino, piperiodino, piperazinyl or morpholino group, the substituent on the heterocyclic being one or two lower alkyl groups; $R_3$ is hydrogen, lower alkyl, halogen or lower alkoxy; X is oxygen (—O—) or sulfur (—S—); and salts thereof.

The foregoing symbols have the same meaning throughout this specification.

DETAILED DESCRIPTION OF THE INVENTION

It has been found that certain intermediates described in parent application Ser. No. 628,277, filed Nov. 3, 1975, now U.S. Pat. No. 3,994,893 i.e., those compounds of formula I having a lower alkoxy group in the 4-position, themselves have antiinflammatory effects as do certain new analogs thereof. This invention relates to those groups of compounds.

The various groups represented by the symbols are of the following kind:

The lower alkyl groups are straight or branched chain hydrocarbon groups having up to seven carbon atoms in the chain, e.g., methyl, ethyl, propyl, isopropyl, butyl, isobutyl, t-butyl, amyl, hexyl, heptyl, etc. The $C_1$-$C_4$ lower alkyl groups and expecially $C_1$-$C_2$ groups are preferred.

The phenyl-lower alkylene groups have a phenyl group attached to an alkyl chain such as those described. The same carbon preferences apply especially to phenylmethyl and phenylethyl.

The halogens are the four common halogens, but chlorine and bromine are preferred, especially the first.

The amino-lower alkylene groups referred to above are preferably linked to the ring through an oxygen atom, e.g., X is oxygen. They have the group

attached to an alkylene chain like those described above with the $C_2$-$C_4$ and $C_2$-$C_3$ alkylene chains constituting preferred and especially preferred groups, respectively. $R_4$ and $R_5$ each is hydrogen or lower alkyl or together with the nitrogen complete an unsubstituted or substituted heterocyclic of the group pyrrolidine, piperidine, piperazine or morpholine, each of which may bear one or two methyl groups. Such amino-lower alkylene groups include, for example, aminoethyl, aminopropyl, methylaminoethyl, methylaminopropyl, ethylaminoethyl, propylaminoethyl, isopropylaminoethyl, dimethylaminoethyl, dimethylaminopropyl, diethylaminoethyl, dipropylaminoethyl, methylethylaminoethyl, piperidinomethyl, piperidinoethyl, pyrrolidinomethyl, pyrrolidinoethyl, piperazin-1-ylmethyl, 2-piperazine-1-ylethyl, morpholinomethyl, 2-morpholinoethyl, 4-methylpiperazine-1-ylmethyl, 4-hydroxyethylpiperazine-1-ylmethyl, 4-methylpiperidinomethyl, etc.

The products of the examples are preferred embodiments.

Especially preferred compounds of formula I are those wherein $R_1$ is lower alkyl, especially ethyl;

$R_2$ is hydrogen or lower alkyl, especially hydrogen, methyl or ethyl;

$R_3$ is hydrogen or lower alkyl, especially hydrogen;

X is oxygen or sulfur, especially oxygen.

The compounds of formula I are produced from a 2-nitrophenylhydrazine of the formula

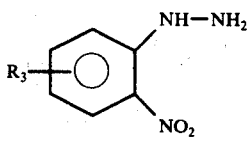

(II)

(produced by the method described in U.S. Pat. No. 3,369,897, Feb. 20, 1968) which is made to react with an alkoxymethyleneoxalacetic acid ester of the formula

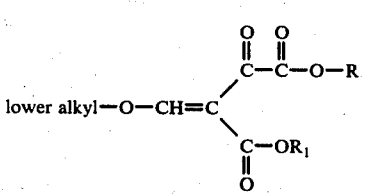

(III)

wherein R and $R_1$ each is lower alkyl, preferably ethyl, e.g., by heating at a temperature about reflux temperature in glacial acetic acid. The resulting compound of the formula

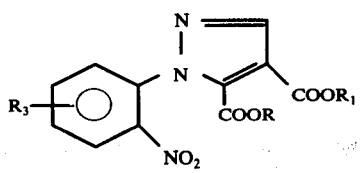

(IV)

is hydrogenated in the presence of catalyst like palladium on carbon in glacial acetic acid or an alcohol like ethanol or butanol, producing a compound of the formula

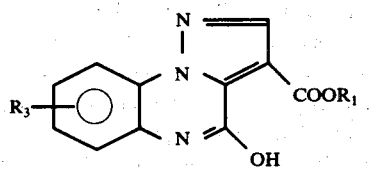

(V)

(or its keto form).

The intermediate of formula V is halogenated with a halogenating agent, e.g., a phosphorus oxyhalide like phosphorus oxychloride to produce a compound of the formula

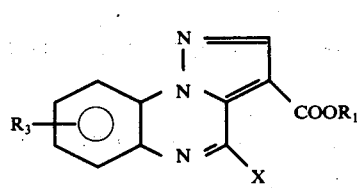

(VI)

wherein X is halogen (preferably chlorine or bromine).

The compound of formula VI is then treated with a compound of the formula $R_2XH$ (VII)

preferably a metal salt thereof like an alkali metal or alkaline earth metal salt. Such reactants include, for example an alkali metal alkoxide like sodium methoxide, potassium ethoxide or the like or an alkali metal salt of a mercptan like the sodium salt of methyl mercptan, etc. The reaction is effected by heating in an inert solvent to obtain the desired product of formula I.

The ester is converted to the acid ($R_1$=H) by hydrolysis, e.g., with an equivalent of base like sodium or potassium hydroxide in an alcohol like ethanol.

Basic compounds of formula I, e.g., those having an amino-lower alkylene group, form salts which are also part of this invention. The salts include acid addition salts, particularly the non-toxic, physiologically acceptable members. These salts are formed by reaction with one or more equivalents of any of a variety or inorganic and organic acids, especially the strong acids, providing acid addition salts including, for example, hydrohalides (especially hydrochloride and hydrobromide), sulfate, nitrate, borate, phosphate, oxalate, tartrate, maleate, citrate, acetate, ascorbate, succinate or aryl- or alkanesulfonates like benzenesulfonate, methanesulfonate, cyclohexanesulfamate and toluenesulfonate. The acid additon salts frequently provide a convenient means for isolating the product, e.g., by forming and precipitating a salt (which is not necessarily non-toxic) in an appropriate medium in which the salt is insoluble, then after separation of the salt, neutralizing with an equivalent of base such as barium hydroxide or sodium hydroxide, to obtain the free base of formula I. Other salts can be formed from the free base by reaction with one or more equivalents of acid containing the desired anion.

Certain members, i.e., wherein $R_1$ is hydrogen, form salts with metals, e.g., alkali metals like sodium, alkaline earth metals like calcium and magnesium, etc., e.g., by treating an ester, i.e., $R_1$ is lower alkyl, with an excess of base. These preferred salts are useful to form soluble derivatives or as intermediates. They are also within the scope of the invention.

Additional experimental details are found in the examples.

The new compounds of this invention have antiinflammatory properties and are useful for administration orally or parenterally as antiinflammatory agents, for example, to reduce local inflammatory conditions such as those of an edematous nature or resulting from proliferation of connective tissue in various mammalian species such as rats, dogs and the like when given orally or parenterally in dosages of about 5 to 50 mg/kg/day, preferably 5 to 25 mg/kg/day, in single or 2 to 4 divided doses, as indicated by the carageenan edema assay in rats or delayed hypersensitivity skin reaction test.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I or physioligically acceptable salt (preferably acid addition salt) is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can also be applied topically as antiinflammatory agents formulated in a conventional lotion, ointment, or cream containing about 0.1 to 3 percent by weight of a compound of formula I or its salt.

The following examples are illustrative of the invention and constitute preferred embodiments. They also serve as models for the preparation of other members of the group which can be produced by suitable substitution of starting materials. All temperatures are in degrees celsuis.

EXAMPLE 1 a. 1-(2-Nitrophenyl)-1H-pyrazole-4,5-dicarboxylic acid, diethyl ester 5 g. of 2-nitrophenylhydrazine are dissolved in 50 ml. of glacial acetic acid and 7.9 g. of ethoxymethyleneoxalacetic acid ethyl ester in 50 ml. of glacial acetic acid are slowly added dropwise. After the addition has been completed, the reaction mixture is refluxed for at least 3 hours. After cooling, the solvent is distilled off first under water vacuum and then under oil pump vacuum. The dark, oily residue is dissolved in 20 ml. of tetrahydrofuran, 10 ml. of ether are added and the mixture is kept in the refrigerator for 24 hours. The product, 1-(2-nitrophenyl)-1H-pyrazole-4,5-dicarboxylic acid, diethyl ester, is obtained in the form of large crystals, yield 11.5 g. The produce is recrystallized from cyclohexane and obtained as yellow crystals; yield 9.8 g., m.p. 45°-46°.

b. 4-Hydroxypyrazolo [1,5-a]quinoxaline-3-carboxylic acid, ethyl ester 50 g. of the product of part a are dissolved in 400 ml. of glacial acetic acid and hydrogenated at 65° in the presence of 0.2 g. of palladium on carbon. At the end of the hydrogen uptake, the mixture is filtered, the solvent is distilled off and the residue is recrystallized from dioxane containing activated carbon to obtain 4-hydroxypyrazolo[1,5-a]quinoxaline-3-carboxylic acid, ethyl ester as white, matted needles; yield 28 g., m.p. 249°-251°.

EXAMPLE 2

4-Chloropyrazolo[1,5-a]quinozalline-3-carboxylic acid, ethyl ester 50 g. of the product of Example 1, part b in 200 ml. of phosphorus oxychloride are refluxed for three hours. After distilling off the excess phosphorus oxychloride, 4-chloropyrazolo[1,5-a]quinoxaline-3-carboxylic acid, ethyl ester crystallizes. The distillation residue is stirred shortly with ice water and then the crude product is filtered off. The crude produce is dried briefly over potassium hydroxide and recrystallized from acetone. The pure product is obtained as white needles; yield 39.5 g., m.p. 105°-106°.

EXAMPLE 3

4-(Ethoxy)pyrazolo[1,5-a]quinoxaline-3-carboxylic acid, ethyl ester a. 5.5 g. of 4-chloropyrazolo[1,5-a]quinozaline-3-carboxylic acid, ethyl ester is heated for two hours with 10 ml. of a 2 molar sodium ethylate solution. The hot reaction solution is filtered and, upon cooling, 4-ethoxypyrazolo[1,5-a]quinoxaline-3-carboxylic acid, ethyl ester crystallizes in the form of white needles. The product is recrystallized from ethanol to obtain 3.4 g. of white crystals, m.p. 88°-90°.

b. 4-Ethoxypyrazolo[1,5-a]quinoxaline-3-carboxylic acid

To a solution of 2.85 g. of 4-ethoxypyrazolo[1,5-a]-quinoxalline-3-carboxylic acid, ethyl ester in hot ethanol, there is added 10 ml. of 10% aqueous sodium hydroxide and the mixture refluxed for 2 hours. The mixture is concentrated under reduced pressure and the residue dissolved in water. The solution is filtered and neutralized with dilute hydrochloric acid. The precipitated 4-ethoxypyrazolo[1,5-a]-quinoxaline-3-carboxylic acid is filtered and washed with a small amount of cold water. The product is crystallized from ethanol.

c. 4-Ethoxypyrazolo[1,5-a]quinoxaline-3-carboxylic acid, sodium salt 2.57 g. of 4-ethoxypyrazolo[1,5-a]quinoxaline-3-carboxylic acid is dissolved in 100 ml. of 0.1N aqueous sodium hydroxide, the solution is filtered and lyophilized to give 4-ethoxypyrazolo[1,5-a]quinoxaline-3-carboxylic acid, sodium salt.

EXAMPLE 4

4-[3-Dimethylamino)propoxy]pyrazolo[1,5-a]quinoxaline-3-carboxylic acid, ethyl ester A solution of 2.76 g. of 4-chloropyrazolo[1,5-a]-quinoxaline-3-carboxylic acid, ethyl ester in benzene is added dropwise, at 10° to a stirred solution of 1.03 g. of 3-dimethylamino-1-propanol and 0.64 g. of butyl lithium in 30 ml. of benzene. The reaction mixture is heated under refllux for 3 hours and is then filtered and concentrated under reduced pressure. The oily residue is dissolved in petroleum ether, treated with carbon and cooled for 12 hours in the refrigerator. The product, 4-[3-(dimethylamino)-propoxy]pyrazolo[1,5-a]quinoxaline-3-carboxylic acid, ethyl ester, crystallizes in the form of white needles, m.p. 78°-81°.

EXAMPLE 5

4,5-Dihydro-4-thioxopyrazolo[1,5-a]quinoxaline-3-carboxylic acid, ethyl ester 8.28 g. of 4-chloropyrazolo[1,5-a]quinoxaline-3-carboxylic acid, ethyl ester are heated at 80° for 1 hour with 2.22 g. of NaHS.H$_2$O and 20 ml. of dimethylformamide. On cooling, the product 4,5-dihydro-4-thioxopyrazolo[1,5-a]-quinoxaline-3-carboxylic acid, ethyl ester crystallizes and it is recrystallized from dimethylformamide-ethanol as yellow needles, m.p. 270-272°.

EXAMPLE 6

4-(Methylthio)pyrazolo[1,5-a]quinoxaline-3-carboxylic acid, ethyl ester 2.76 g. of 4-chloropyrazolo[1,5-a]quinoxaline-3-carboxylic acid ethyl ester are heated with 0.71 g. of the sodium salt of methyl mercaptan in dimethylformamide. After cooling, the reaction mixture is poured into water. The product 4-(methylthio)pyrazolo[1,5-a]quinoxaline-3-carboxylic acid, ethyl ester is filtered under suction and crystallized from ethanol as white needles, m.p. 97°-98°.

The following additional products are obtained by the procedure of Example 3 by substituting for the sodium ethylate the sodium salt of the R$_2$XH compound shown in the first column and, if desired, substituting an R$_3$-substituted nitrophenylhydrazine for the 2nitrophenylhydrazine in Example 1, part a. The free acids and salts (R$_1$ = H or Na or K) are obtained as in Example 3, parts b and c, respectively.

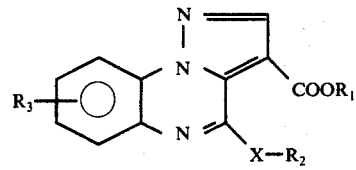

| Example | R$_2$XH | R$_1$ | R$_2$X | R$_3$ |
| --- | --- | --- | --- | --- |
| 7 | C$_2$H$_5$OH | CH$_3$ | C$_2$H$_5$O— | H |

-continued

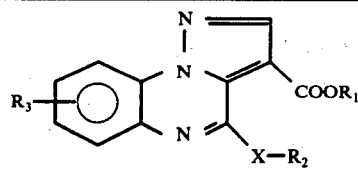

| Example | R₂XH | R₁ | R₂X | R₃ |
|---|---|---|---|---|
| 8 | $C_2H_5OH$ | H | $C_2H_5O-$ | 7-Cl |
| 9 | $C_4H_9OH$ | $C_2H_5$ | $C_4H_9O-$ | 8-$CH_3$ |
| 10 | C₆H₅-CH₂OH | $C_2H_5$ | C₆H₅-CH₂O- | 8-Br |
| 11 | $CH_3N$⟨piperazine⟩$NCH_2CH_2OH$ | $C_2H_5$ | $CH_3N$⟨piperazine⟩$N-CH_2CH_2O-$ | H |
| 12 | $(CH_3)_2NCH_2CH_2OH$ | $C_3H_7$ | $(CH_3)_2NCH_2CH_2O-$ | 6-Br |
| 13 | $NH_2CH_2CH_2OH$ | $C_2H_5$ | $NH_2CH_2CH_2O-$ | 8-$CH_3$ |
| 14 | pyrrolidine-$N-CH_2-CH(CH_2)-OH$ | $C_2H_5$ | pyrrolidine-$N-CH_2CH(CH_2)-O-$ | H |
| 15 | $HN$⟨piperazine⟩$NCH_2CH_2CH_2OH$ | $CH_3$ | $HN$⟨piperazine⟩$N-CH_2CH_2CH_2O-$ | H |
| 16 | 4-$CH_3$-piperidine-$NCH_2OH$ | $C_2H_5$ | 4-$CH_3$-piperidine-$NCH_2O-$ | H |
| 17 | 3,5-di-$CH_3$-piperidine-$NCH_2OH$ | $C_2H_5$ | 3,5-di-$CH_3$-piperidine-$NCH_2O-$ | H |
| 18 | C₆H₅-$CH_2CH_2OH$ | Na | C₆H₅-$CH_2CH_2O-$ | 9-Cl |
| 19 | C₆H₅-$CH_2SH$ | $C_4H_9$ | C₆H₅-$CH_2S-$ | H |
| 20 | C₆H₅-$CH_2CH_2SH$ | $C_2H_5$ | C₆H₅-$CH_2CH_2S-$ | H |
| 21 | $C_4H_9SH$ | $C_2H_5$ | $C_4H_9S-$ | H |
| 22 | $C_3H_7SH$ | $CH_3$ | $C_3H_7S-$ | 7-Cl |
| 23 | $C_2H_5SH$ | $C_2H_5$ | $C_2H_5S-$ | 8-$CH_3$ |
| 24 | $C_5H_{11}CH(CH_3)OH$ | $C_2H_5$ | $C_5H_{11}CH(CH_3)O-$ | H |
| 25 | $(CH_3)_2CHOH$ | H | $(CH_3)_2CHO-$ | H |
| 26 | $CH_3-N$⟨piperazine⟩$NCH_2CH_2OH$ | H | $CH_3-N$⟨piperazine⟩$NCH_2CH_2O-$ | 8-$OCH_3$ |
| 27 | $(CH_3)_2NCH_2CHOH$ | $C_2H_5$ | $(CH_3)_2NCH_2CH_2-O-$ | 8-$OC_2H_5$ |
| 28 | $(C_4H_9)_2NCH_2CH_2OH$ | H | $(C_4H_9)_2NCH_2CH_2O-$ | H |

-continued

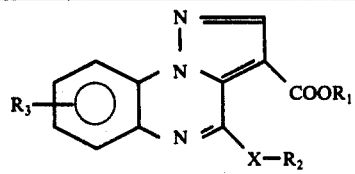

| Example | $R_2XH$ | $R_1$ | $R_2X$ | $R_3$ |
|---------|---------|-------|--------|-------|
| 29 | 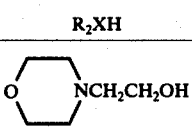 | H | 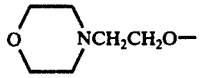 | H |

What is claimed is:
1. A compound of the formula

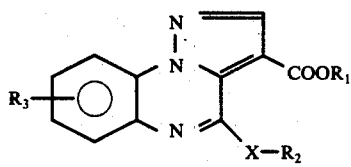

wherein
$R_1$ is hydrogen or lower alkyl;
$R_2$ is hydrogen, lower alkyl, phenyl-lower alkylene or

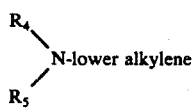

wherein
$R_4$ and $R_5$ each is hydrogen or lower alkyl or together with the nitrogen complete one of the heterocyclics pyrrolidion, piperidino, said heterocyclics being unsubstituted or substituted with one or two lower alkyl groups;
$R_3$ is hydrogen, lower alkyl, halogen or lower alkoxy;
X is oxygen or sulfur;
and salts thereof.
2. A compound as in claim 1 wherein X is oxygen.
3. A compound as in claim 1 wherein X is sulfur.
4. A compound as in claim 1 wherein $R_1$ and $R_2$ each is hydrogen or lower alkyl; $R_3$ is hydrogen and X is sulfur or oxygen.
5. A compound as in claim 1 wherein $R_1$ is lower alkyl; $R_2$ is hydrogen or lower alkyl; $R_3$ is hydrogen and X is oxygen or sulfur.
6. A compound as in claim 1 wherein $R_2$—X is di-lower alkylamino-lower alkoxy.
7. A compound as in claim 1 wherein $R_3$ is hydrogen.
8. A compound as in claim 7 wherein $R_1$ is ethyl and $R_2$—X is hydroxy.
9. A compound as in claim 7 wherein $R_1$ is ethyl and $R_2$—X is mercapto.
10. A compound as in claim 7 wherein $R_1$ is ethyl and $R_2$—X is ethoxy.
11. A compound as in claim 7 wherein $R_1$ is ethyl and $R_2$—X is dimethylaminopropoxy.
12. A compound as in claim 7 wherein $R_1$ is ethyl and $R_2$—X is methylthio.

* * * * *